US005518897A

United States Patent [19]

Stevens, Jr. et al.

[11] Patent Number: 5,518,897
[45] Date of Patent: May 21, 1996

[54] RECOMBINANT BIOPESTICIDE AND METHOD OF USE THEREOF

[75] Inventors: S. Edward Stevens, Jr., Arlington; Randy C. Murphy, Memphis, both of Tenn.

[73] Assignee: Memphis State University, Memphis, Tenn.

[21] Appl. No.: 188,581

[22] Filed: Jan. 28, 1994

Related U.S. Application Data

[63] Continuation-in-part of Ser. No. 877,876, May 4, 1992, abandoned.

[51] Int. Cl.[6] .............................. C12P 21/06; C12N 1/20; A01N 63/00; A01N 65/00

[52] U.S. Cl. .................. 435/69.1; 435/252.3; 435/252.5; 435/320.1; 435/832; 424/93.1; 424/93.2; 424/93.4; 424/93.461; 536/22.1; 536/23.1; 536/23.4; 536/23.7; 536/23.71
[58] Field of Search ................................ 435/69.1, 252.3, 435/252.5, 320.1, 832; 424/93 L, 93.1, 93.2, 93.4, 93.461; 536/22.1, 23.1, 23.4, 23.7, 23.71

[56] References Cited

FOREIGN PATENT DOCUMENTS

| | | |
|---|---|---|
| WO8806631 | 9/1988 | WIPO . |
| WO8907605 | 8/1989 | WIPO . |

OTHER PUBLICATIONS

Delécluse et al., Deletion by In Vivo Recombination Shows that the 28–Kilodalton Cytolytic Polypeptide from *Bacillus thuringiensis subsp. israelnesis Is Not Essential for Mosquitocidal Activity, Journal of Bacteriology*, vol. 173, No. 11, pp. 3374–3381 (Jun. 1981).

Murphy et al., Purpose of the Project To Produce a Mosquitocidal Cyanobacterium That Can Successfully Compete in Mosquito Breeding Locales, May 6, 1991, Meeting of the American Society for Microbiology, Dallas, Texas.

Murphy et al., Nucleotide Sequence and Further Characterization of the Synechococcus sp. Strain PCC 7002 recA Gene: Complementation of a Cyanobacterial recA Mutation by the Escherichia coli recA Gene, Journal of Bacteriology, vol. 172, No. 2, pp. 967–976 (Feb. 1990).

Chungjatupornchai, Expression of the Mosquitocidal–Protein Genes of *Bacillus thuringiensis* subsp. israelensis and the Herbicide–Resistance Gene bar in Synechocystis PCC6803, Current Microbiology, vol. 21, pp. 283–288 (1990).

Angsuthanasombat et al., Biosynthesis of 130–Kioldalton Mosquito Larvicide in the Cyanobacterium Agmenellum quadruplicatum PR–6, Applied and Environmental Microbiology, vol. 55, No. 9, pp. 2428–2430 (Sep. 1989).

Höfte et al., Insecticidal Crystal Proteins of *Bacillus thuringiensis,* Microbiological Reviews, vol. 53, No. 2, pp. 242–255 (Jun. 1989).

Chilcott et al., Comparative Toxicity of *Bacillus thuringiensis* var. israelensis Crystal Proteins in vivo and in vitro, Journal of General Microbiology, 134, pp. 2551–2558 (1988).

Donovan et al., Molecular Characterization of a Gene Encoding a 72–Kilodalton Mosquito–Toxic Crystal Protein from *Bacillus thuringiensis* subsp. israelensis, Journal of Bacteriology, vol. 170, No. 10, pp. 4732–4738 (Oct. 1988).

Aronson et al., *Bacillus thuringiensis* and Related Insect Pathogens, Microbiological Reviews, vol. 50, No. 1, pp. 1–24 (Mar. 1986).

Buzby et al., Expression of the *Escherichia coli* lacZ Gene on a Plasmid Vector in a Cyanobacterium, Science, vol. 230, pp. 805–807 (Nov. 1985).

Angsuthanasombat et al. "Cloning and Expression of 130–kd mosquito–larvicidal δ–endotoxin gene of *Bacillus thuringiensis* var. Israelensis in *Escherichia coli*", Mol. Gen. Genet. (1987) 208:384–389.

Glover "Expression of cloned DNAs in E. coli plasmids" *Gene Cloning* (1984) pp. 110–126.

*Primary Examiner*—Charles L. Patterson, Jr.
*Assistant Examiner*—Hyosuk Kim
*Attorney, Agent, or Firm*—Dilworth & Barrese

[57] ABSTRACT

A recombinantly derived biopesticide active against Diptera includes cyanobacteria transformed with a plasmid containing a *B. thuringiensis* subsp. *israelensis* dipteracidal protein translationally fused to a strong, highly active native cyanobacterial regulatory gene sequence.

30 Claims, 8 Drawing Sheets

```
PCR Primer   5'-CGCAGCTCGCGTCGACTCCCG
                                    G
         10        20        30      GTGGAAGATAGTTCTTTAGA
TTTAAAATAAAAAAATTCAATAAAAGGTGGAATGAATTATATGGAAGATAGTTCTTTAGA
                                      METGluAspSerSerLeuAs TAC-3'   70        80        90       100       110       120
TACTTTAAGTATAGTTAATGAAACAGACTTTCCATTATATAATAATTATACCGAACCTAC
pThrLeuSerIleValAsnGluThrAspPheProLeuTyrAsnAsnTyrThrGluProTh 130       140       150       160       170       180
TATTGCGCCAGCATTAATAGCAGTAGCTCCCATCGCACAATATCTTGCAACAGCTATAGG
rIleAlaProAlaLeuIleAlaValAlaProIleAlaGlnTyrLeuAlaThrAlaIleGl 190       200       210       220       230       240
GAAATGGGCGGCAAAGGCAGCATTTTCAAAAGTACTATCACTTATATTCCCAGGTTCTCA
yLysTrpAlaAlaLysAlaAlaPheSerLysValLeuSerLeuIlePheProGlySerGl 250       260       270       280       290       300
ACCTGCTACTATGGAAAAGTTCGTACAGAAGTGGAAACACTTATAAATCAAAAATTAAG
nProAlaThrMETGluLysValArgThrGluValGluThrLeuIleAsnGlnLysLeuSe 310       320       330       340       350       360
CCAAGATCGAGTCAATATATTAAACGCAGAATATAGGGGGATTATTGAGGTTAGTGATGT
rGlnAspArgValAsnIleLeuAsnAlaGluTyrArgGlyIleIleGluValSerAspVa 370       380       390       400       410       420
ATTTGATGCGTATATTAAACAACCAGGTTTTACCCCTGCAACAGCCAAGGGTTATTTTCT
lPheAspAlaTyrIleLysGlnProGlyPheThrProAlaThrAlaLysGlyTyrPheLe 430       440       450       460       470       480
AAATCTAAGTGGTGCTATAATACAACGATTACCTCAATTTGAGGTTCAAACATATGAAGG
uAsnLeuSerGlyAlaIleIleGlnArgLeuProGlnPheGluValGlnThrTyrGluGl 490       500       510       520       530       540
AGTATCTATAGCACTTTTTACTCAAATGTGTACACTTCATTTAACTTTATTAAAAGACGG
yValSerIleAlaLeuPheThrGlnMETCysThrLeuHisLeuThrLeuLeuLysAspGl 550       560       570       580       590       600
AATCCTAGCAGGGAGTGCATGGGGATTTACTCAAGCTGATGTAGATTCATTTATAAAATT
yIleLeuAlaGlySerAlaTrpGlyPheThrGlnAlaAspValAspSerPheIleLysLe 610       620       630       640       650       660
ATTTAATCAAAAAGTATTAGATTACAGGACCAGATTAATGAGAATGTACACAGAAGAGTT
uPheAsnGlnLysValLeuAspTyrArgThrArgLeuMETArgMETTyrThrGluGluPh 670       680       690       700       710       720
CGGAAGATTGTGTAAAGTCAGTCTTAAAGATGGATTGACGTTCCGGAATATGTGTAATTT
eGlyArgLeuCysLysValSerLeuLysAspGlyLeuThrPheArgAsnMETCysAsnLe 730       740       750       760       770       780
ATATGTGTTTCCATTTGCTGAAGCCTGGTCTTTAATGAGATATGAAGGATTAAAATTACA
uTyrValPheProPheAlaGluAlaTrpSerLeuMETArgTyrGluGlyLeuLysLeuGl
```

*FIG. 2A*

```
       790       800       810       820       830       840
AAGCTCTCTATCATTATGGGATTATGTTGGTGTCTCAATTCCTGTAAATTATAATGAATG
nSerSerLeuSerLeuTrpAspTyrValGlyValSerIleProValAsnTyrAsnGluTr 850       860       870       880       890       900
GGGAGGACTAGTTTATAAGTTATTAATGGGGAAGTTAATCAAAGATTAACAACTGTTAA
pGlyGlyLeuValTyrLysLeuLeuMETGlyGluValAsnGlnArgLeuThrThrValLy 910       920       930       940       950       960
ATTTAATTATTCTTTCACTAATGAACCAGCTGATATACCAGCAAGAGAAAATATTCGTGG
sPheAsnTyrSerPheThrAsnGluProAlaAspIleProAlaArgGluAsnIleArgGl 970       980       990      1000      1010      1020
CGTCCATCCTATATACGATCCTAGTTCTGGGCTTACAGGATGGATAGGAAACGGAAGAAC
yValHisProIleTyrAspProSerSerGlyLeuThrGlyTrpIleGlyAsnGlyArgTh 1030      1040      1050      1060      1070      1080
AAACAATTTTAATTTTGCTGATAACAATGGCAATGAAATTATGGAAGTTAGAACACAAAC
rAsnAsnPheAsnPheAlaAspAsnAsnGlyAsnGluIleMETGluValArgThrGlnTh 1090      1100      1110      1120      1130      1140
TTTTTATCAAAATCCAAATAATGAGCCTATAGCGCCTAGAGATATTATAAATCAAATTTT
rPheTyrGlnAsnProAsnAsnGluProIleAlaProArgAspIleIleAsnGlnIleLe 1150      1160      1170      1180      1190      1200
AACTGCGCCAGCACCAGCAGACCTATTTTTTAAAAATGCAGATATAAATGTAAAGTTCAC
uThrAlaProAlaProAlaAspLeuPhePheLysAsnAlaAspIleAsnValLysPheTh 1210      1220      1230      1240      1250      1260
ACAGTGGTTTCAGTCTACTCTATATGGGTGGAACATTAAACTCGGTACACAAACGGTTTT
rGlnTrpPheGlnSerThrLeuTyrGlyTrpAsnIleLysLeuGlyThrGlnThrValLe 1270      1280      1290      1300      1310      1320
AAGTAGTAGAACCGGAACAATACCACCAAATTATTTAGCATATGATGGATATTATATTCG
uSerSerArgThrGlyThrIleProProAsnTyrLeuAlaTyrAspGlyTyrTyrIleAr 1330      1340      1350      1360      1370      1380
TGCTATTTCAGCTTGCCCAAGAGGAGTCTCACTTGCATATAATCACGATCTTACAACACT
gAlaIleSerAlaCysProArgGlyValSerLeuAlaTyrAsnHisAspLeuThrThrLe 1390      1400      1410      1420      1430      1440
AACATATAATAGAATAGAGTATGATTCACCTACTACAGAAAATATTATTGTAGGGTTTGC
uThrTyrAsnArgIleGluTyrAspSerProThrThrGluAsnIleIleValGlyPheAl 1450      1460      1470      1480      1490      1500
ACCAGATAATACTAAGGACTTTTATTCTAAAAAATCTCACTATTTAAGTGAAACGAATGA
aProAspAsnThrLysAspPheTyrSerLysLysSerHisTyrLeuSerGluThrAsnAs 1510      1520      1530      1540      1550      1560
TAGTTATGTAATTCCTGCTCTGCAATTTGCTGAAGTTTCAGATAGATCATTTTTAGAAGA
pSerTyrValIleProAlaLeuGlnPheAlaGluValSerAspArgSerPheLeuGluAs
```

FIG. 2B

```
       1570      1580      1590      1600      1610      1620
TACGCCAGATCAAGCAACAGACGGCAGTATTAAATTTGCACGTACTTTCATTAGTAATGA
pThrProAspGlnAlaThrAspGlySerIleLysPheAlaArgThrPheIleSerAsnGl 1630      1640      1650      1660      1670      1680
AGCTAAGTACTCTATTAGACTAAACACCGGGTTTAATACGGCAACTAGATATAAATTAAT
uAlaLysTyrSerIleArgLeuAsnThrGlyPheAsnThrAlaThrArgTyrLysLeuIl 1690      1700      1710      1720      1730      1740
TATCAGGGTAAGAGTACCTTATCGCTTACCTGCTGGAATACGGGTACAATCTCAGAATTC
eIleArgValArgValProTyrArgLeuProAlaGlyIleArgValGlnSerGlnAsnSe 1750      1760      1770      1780      1790      1800
gggaaataatagaatgctaggcagtttttactgcaaatgctaatccagaatgggtggattt
rGlyAsnAsnArgMETLeuGlySerPheThrAlaAsnAlaAsnProGluTrpValAspPh 1810      1820      1830      1840      1850      1860
TGTCACAGATGCATTTACATTTAACGATTTAGGGATTACAACTTCAAGTACAAATGCTTT
eValThrAspAlaPheThrPheAsnAspLeuGlyIleThrThrSerSerThrAsnAlaLe 1870      1880      1890      1900      1910      1920
ATTTAGTATTTCTTCAGATAGTTTAAATTCTGGAGAAGAGTGGTATTTATCGCAGTTGTT
uPheSerIleSerSerAspSerLeuAsnSerGlyGluGluTrpTyrLeuSerGlnLeuPh 1930      1940      1950      1960      1970      1980
TTTAGTAAAAGAATCGGCCTTTACGACGCAAATTAATCCGTTACTAAAGTAGAAGTCATG
eLeuValLysGluSerAlaPheThrThrGlnIleAsnProLeuLeuLysEND    3'-C 1990      2000      2010      2020      2030      2040
TTAGCACAAGAGGAGTGAGTATTGTGGCTCCTCTTGTAATTTTAATCGCTAATATTTCTA
AATCGTGTTCTCCTCACTCA
                    G
                   C
                  T
                   TGAACAGCGCTCGTAGC-5'    PCR Primer
```

FIG. 2C

```
                              ──────── cryIVD ────────

5'  -  TCGACTCCCGGGTGGAAGATAGTTCTTTAGATACTTTAAGTATAGTT---
   3'- GAGGGCCCACCTTCTATCAAGAAATCTATGAAATTCATATCAA---

GluAspSerSerLeuAspThrLeuSerIleVal---
```

FIG. 3

```
                                       SalI
5'———— cpcB ————————            ╲               5'———— cryIVD ———— 3'
ATG TTT GAT ATT TTT ACC CGG GGA TCC GTC GAC TCC CGG GTG AAA GAT AGT TCT TTA MET PHE ASP ILE PHE THR arg gly ser val asp ser arg val GLU ASP SER SER LEU
```

FIG. 4

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 2040 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 41..1969

( x i ) SEQUENCE DESCRIPTION: SEQ ID NO:1:

```
TTTAAAATAA AAAAATTCAA TAAAAGGTGG AATGAATTAT ATG GAA GAT AGT TCT      55
                                           Met Glu Asp Ser Ser
                                             1               5

TTA GAT ACT TTA AGT ATA GTT AAT GAA ACA GAC TTT CCA TTA TAT AAT     103
Leu Asp Thr Leu Ser Ile Val Asn Glu Thr Asp Phe Pro Leu Tyr Asn
                 10                  15                  20

AAT TAT ACC GAA CCT ACT ATT GCG CCA GCA TTA ATA GCA GTA GCT CCC     151
Asn Tyr Thr Glu Pro Thr Ile Ala Pro Ala Leu Ile Ala Val Ala Pro
             25                  30                  35

ATC GCA CAA TAT CTT GCA ACA GCT ATA GGG AAA TGG GCG GCA AAG GCA     199
Ile Ala Gln Tyr Leu Ala Thr Ala Ile Gly Lys Trp Ala Ala Lys Ala
         40                  45                  50

GCA TTT TCA AAA GTA CTA TCA CTT ATA TTC CCA GGT TCT CAA CCT GCT     247
Ala Phe Ser Lys Val Leu Ser Leu Ile Phe Pro Gly Ser Gln Pro Ala
     55                  60                  65

ACT ATG GAA AAA GTT CGT ACA GAA GTG GAA ACA CTT ATA AAT CAA AAA     295
Thr Met Glu Lys Val Arg Thr Glu Val Glu Thr Leu Ile Asn Gln Lys
 70                  75                  80                  85

TTA AGC CAA GAT CGA GTC AAT ATA TTA AAC GCA GAA TAT AGG GGG ATT     343
Leu Ser Gln Asp Arg Val Asn Ile Leu Asn Ala Glu Tyr Arg Gly Ile
                 90                  95                 100

ATT GAG GTT AGT GAT GTA TTT GAT GCG TAT ATT AAA CAA CCA GGT TTT     391
Ile Glu Val Ser Asp Val Phe Asp Ala Tyr Ile Lys Gln Pro Gly Phe
```

|     |     |     |     |     | 105 |     |     |     |     | 110 |     |     |     |     | 115 |     |      |
| --- | --- | --- | --- | --- | --- | --- | --- | --- | --- | --- | --- | --- | --- | --- | --- | --- | ---- |
| ACC | CCT | GCA | ACA | GCC | AAG | GGT | TAT | TTT | CTA | AAT | CTA | AGT | GGT | GCT | ATA |     | 439  |
| Thr | Pro | Ala | Thr | Ala | Lys | Gly | Tyr | Phe | Leu | Asn | Leu | Ser | Gly | Ala | Ile |     |      |
|     |     | 120 |     |     |     |     | 125 |     |     |     |     | 130 |     |     |     |     |      |
| ATA | CAA | CGA | TTA | CCT | CAA | TTT | GAG | GTT | CAA | ACA | TAT | GAA | GGA | GTA | TCT |     | 487  |
| Ile | Gln | Arg | Leu | Pro | Gln | Phe | Glu | Val | Gln | Thr | Tyr | Glu | Gly | Val | Ser |     |      |
|     | 135 |     |     |     |     | 140 |     |     |     |     | 145 |     |     |     |     |     |      |
| ATA | GCA | CTT | TTT | ACT | CAA | ATG | TGT | ACA | CTT | CAT | TTA | ACT | TTA | TTA | AAA |     | 535  |
| Ile | Ala | Leu | Phe | Thr | Gln | Met | Cys | Thr | Leu | His | Leu | Thr | Leu | Leu | Lys |     |      |
| 150 |     |     |     |     | 155 |     |     |     |     | 160 |     |     |     |     | 165 |     |      |
| GAC | GGA | ATC | CTA | GCA | GGG | AGT | GCA | TGG | GGA | TTT | ACT | CAA | GCT | GAT | GTA |     | 583  |
| Asp | Gly | Ile | Leu | Ala | Gly | Ser | Ala | Trp | Gly | Phe | Thr | Gln | Ala | Asp | Val |     |      |
|     |     |     |     | 170 |     |     |     |     | 175 |     |     |     |     | 180 |     |     |      |
| GAT | TCA | TTT | ATA | AAA | TTA | TTT | AAT | CAA | AAA | GTA | TTA | GAT | TAC | AGG | ACC |     | 631  |
| Asp | Ser | Phe | Ile | Lys | Leu | Phe | Asn | Gln | Lys | Val | Leu | Asp | Tyr | Arg | Thr |     |      |
|     |     |     | 185 |     |     |     |     | 190 |     |     |     |     | 195 |     |     |     |      |
| AGA | TTA | ATG | AGA | ATG | TAC | ACA | GAA | GAG | TTC | GGA | AGA | TTG | TGT | AAA | GTC |     | 679  |
| Arg | Leu | Met | Arg | Met | Tyr | Thr | Glu | Glu | Phe | Gly | Arg | Leu | Cys | Lys | Val |     |      |
|     |     | 200 |     |     |     |     | 205 |     |     |     |     | 210 |     |     |     |     |      |
| AGT | CTT | AAA | GAT | GGA | TTG | ACG | TTC | CGG | AAT | ATG | TGT | AAT | TTA | TAT | GTG |     | 727  |
| Ser | Leu | Lys | Asp | Gly | Leu | Thr | Phe | Arg | Asn | Met | Cys | Asn | Leu | Tyr | Val |     |      |
|     | 215 |     |     |     |     | 220 |     |     |     |     | 225 |     |     |     |     |     |      |
| TTT | CCA | TTT | GCT | GAA | GCC | TGG | TCT | TTA | ATG | AGA | TAT | GAA | GGA | TTA | AAA |     | 775  |
| Phe | Pro | Phe | Ala | Glu | Ala | Trp | Ser | Leu | Met | Arg | Tyr | Glu | Gly | Leu | Lys |     |      |
| 230 |     |     |     |     | 235 |     |     |     |     | 240 |     |     |     |     | 245 |     |      |
| TTA | CAA | AGC | TCT | CTA | TCA | TTA | TGG | GAT | TAT | GTT | GGT | GTC | TCA | ATT | CCT |     | 823  |
| Leu | Gln | Ser | Ser | Leu | Ser | Leu | Trp | Asp | Tyr | Val | Gly | Val | Ser | Ile | Pro |     |      |
|     |     |     |     | 250 |     |     |     |     | 255 |     |     |     |     | 260 |     |     |      |
| GTA | AAT | TAT | AAT | GAA | TGG | GGA | GGA | CTA | GTT | TAT | AAG | TTA | TTA | ATG | GGG |     | 871  |
| Val | Asn | Tyr | Asn | Glu | Trp | Gly | Gly | Leu | Val | Tyr | Lys | Leu | Leu | Met | Gly |     |      |
|     |     |     | 265 |     |     |     |     | 270 |     |     |     |     | 275 |     |     |     |      |
| GAA | GTT | AAT | CAA | AGA | TTA | ACA | ACT | GTT | AAA | TTT | AAT | TAT | TCT | TTC | ACT |     | 919  |
| Glu | Val | Asn | Gln | Arg | Leu | Thr | Thr | Val | Lys | Phe | Asn | Tyr | Ser | Phe | Thr |     |      |
|     |     | 280 |     |     |     |     | 285 |     |     |     |     | 290 |     |     |     |     |      |
| AAT | GAA | CCA | GCT | GAT | ATA | CCA | GCA | AGA | GAA | AAT | ATT | CGT | GGC | GTC | CAT |     | 967  |
| Asn | Glu | Pro | Ala | Asp | Ile | Pro | Ala | Arg | Glu | Asn | Ile | Arg | Gly | Val | His |     |      |
|     | 295 |     |     |     |     | 300 |     |     |     |     | 305 |     |     |     |     |     |      |
| CCT | ATA | TAC | GAT | CCT | AGT | TCT | GGG | CTT | ACA | GGA | TGG | ATA | GGA | AAC | GGA |     | 1015 |
| Pro | Ile | Tyr | Asp | Pro | Ser | Ser | Gly | Leu | Thr | Gly | Trp | Ile | Gly | Asn | Gly |     |      |
| 310 |     |     |     |     | 315 |     |     |     |     | 320 |     |     |     |     | 325 |     |      |
| AGA | ACA | AAC | AAT | TTT | AAT | TTT | GCT | GAT | AAC | AAT | GGC | AAT | GAA | ATT | ATG |     | 1063 |
| Arg | Thr | Asn | Asn | Phe | Asn | Phe | Ala | Asp | Asn | Asn | Gly | Asn | Glu | Ile | Met |     |      |
|     |     |     |     | 330 |     |     |     |     | 335 |     |     |     |     | 340 |     |     |      |
| GAA | GTT | AGA | ACA | CAA | ACT | TTT | TAT | CAA | AAT | CCA | AAT | AAT | GAG | CCT | ATA |     | 1111 |
| Glu | Val | Arg | Thr | Gln | Thr | Phe | Tyr | Gln | Asn | Pro | Asn | Asn | Glu | Pro | Ile |     |      |
|     |     |     | 345 |     |     |     |     | 350 |     |     |     |     | 355 |     |     |     |      |
| GCG | CCT | AGA | GAT | ATT | ATA | AAT | CAA | ATT | TTA | ACT | GCG | CCA | GCA | CCA | GCA |     | 1159 |
| Ala | Pro | Arg | Asp | Ile | Ile | Asn | Gln | Ile | Leu | Thr | Ala | Pro | Ala | Pro | Ala |     |      |
|     |     | 360 |     |     |     |     | 365 |     |     |     |     | 370 |     |     |     |     |      |
| GAC | CTA | TTT | TTT | AAA | AAT | GCA | GAT | ATA | AAT | GTA | AAG | TTC | ACA | CAG | TGG |     | 1207 |
| Asp | Leu | Phe | Phe | Lys | Asn | Ala | Asp | Ile | Asn | Val | Lys | Phe | Thr | Gln | Trp |     |      |
|     | 375 |     |     |     |     | 380 |     |     |     |     | 385 |     |     |     |     |     |      |
| TTT | CAG | TCT | ACT | CTA | TAT | GGG | TGG | AAC | ATT | AAA | CTC | GGT | ACA | CAA | ACG |     | 1255 |
| Phe | Gln | Ser | Thr | Leu | Tyr | Gly | Trp | Asn | Ile | Lys | Leu | Gly | Thr | Gln | Thr |     |      |
| 390 |     |     |     |     | 395 |     |     |     |     | 400 |     |     |     |     | 405 |     |      |
| GTT | TTA | AGT | AGT | AGA | ACC | GGA | ACA | ATA | CCA | CCA | AAT | TAT | TTA | GCA | TAT |     | 1303 |
| Val | Leu | Ser | Ser | Arg | Thr | Gly | Thr | Ile | Pro | Pro | Asn | Tyr | Leu | Ala | Tyr |     |      |
|     |     |     |     | 410 |     |     |     |     | 415 |     |     |     |     | 420 |     |     |      |
| GAT | GGA | TAT | TAT | ATT | CGT | GCT | ATT | TCA | GCT | TGC | CCA | AGA | GGA | GTC | TCA |     | 1351 |
| Asp | Gly | Tyr | Tyr | Ile | Arg | Ala | Ile | Ser | Ala | Cys | Pro | Arg | Gly | Val | Ser |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 425 |     |     |     |     | 430 |     |     |     |     | 435 |     |      |
| CTT | GCA | TAT | AAT | CAC | GAT | CTT | ACA | ACA | CTA | ACA | TAT | AAT | AGA | ATA | GAG | 1399 |
| Leu | Ala | Tyr | Asn | His | Asp | Leu | Thr | Thr | Leu | Thr | Tyr | Asn | Arg | Ile | Glu |      |
|     |     |     | 440 |     |     |     |     | 445 |     |     |     |     | 450 |     |     |      |
| TAT | GAT | TCA | CCT | ACT | ACA | GAA | AAT | ATT | ATT | GTA | GGG | TTT | GCA | CCA | GAT | 1447 |
| Tyr | Asp | Ser | Pro | Thr | Thr | Glu | Asn | Ile | Ile | Val | Gly | Phe | Ala | Pro | Asp |      |
|     | 455 |     |     |     |     |     | 460 |     |     |     |     | 465 |     |     |     |      |
| AAT | ACT | AAG | GAC | TTT | TAT | TCT | AAA | AAA | TCT | CAC | TAT | TTA | AGT | GAA | ACG | 1495 |
| Asn | Thr | Lys | Asp | Phe | Tyr | Ser | Lys | Lys | Ser | His | Tyr | Leu | Ser | Glu | Thr |      |
| 470 |     |     |     |     | 475 |     |     |     |     | 480 |     |     |     |     | 485 |      |
| AAT | GAT | AGT | TAT | GTA | ATT | CCT | GCT | CTG | CAA | TTT | GCT | GAA | GTT | TCA | GAT | 1543 |
| Asn | Asp | Ser | Tyr | Val | Ile | Pro | Ala | Leu | Gln | Phe | Ala | Glu | Val | Ser | Asp |      |
|     |     |     |     | 490 |     |     |     |     | 495 |     |     |     |     | 500 |     |      |
| AGA | TCA | TTT | TTA | GAA | GAT | ACG | CCA | GAT | CAA | GCA | ACA | GAC | GGC | AGT | ATT | 1591 |
| Arg | Ser | Phe | Leu | Glu | Asp | Thr | Pro | Asp | Gln | Ala | Thr | Asp | Gly | Ser | Ile |      |
|     |     |     | 505 |     |     |     |     | 510 |     |     |     |     | 515 |     |     |      |
| AAA | TTT | GCA | CGT | ACT | TTC | ATT | AGT | AAT | GAA | GCT | AAG | TAC | TCT | ATT | AGA | 1639 |
| Lys | Phe | Ala | Arg | Thr | Phe | Ile | Ser | Asn | Glu | Ala | Lys | Tyr | Ser | Ile | Arg |      |
|     |     | 520 |     |     |     |     | 525 |     |     |     |     | 530 |     |     |     |      |
| CTA | AAC | ACC | GGG | TTT | AAT | ACG | GCA | ACT | AGA | TAT | AAA | TTA | ATT | ATC | AGG | 1687 |
| Leu | Asn | Thr | Gly | Phe | Asn | Thr | Ala | Thr | Arg | Tyr | Lys | Leu | Ile | Ile | Arg |      |
|     | 535 |     |     |     |     | 540 |     |     |     |     | 545 |     |     |     |     |      |
| GTA | AGA | GTA | CCT | TAT | CGC | TTA | CCT | GCT | GGA | ATA | CGG | GTA | CAA | TCT | CAG | 1735 |
| Val | Arg | Val | Pro | Tyr | Arg | Leu | Pro | Ala | Gly | Ile | Arg | Val | Gln | Ser | Gln |      |
| 550 |     |     |     |     | 555 |     |     |     |     | 560 |     |     |     |     | 565 |      |
| AAT | TCG | GGA | AAT | AAT | AGA | ATG | CTA | GGC | AGT | TTT | ACT | GCA | AAT | GCT | AAT | 1783 |
| Asn | Ser | Gly | Asn | Asn | Arg | Met | Leu | Gly | Ser | Phe | Thr | Ala | Asn | Ala | Asn |      |
|     |     |     |     | 570 |     |     |     |     | 575 |     |     |     |     | 580 |     |      |
| CCA | GAA | TGG | GTG | GAT | TTT | GTC | ACA | GAT | GCA | TTT | ACA | TTT | AAC | GAT | TTA | 1831 |
| Pro | Glu | Trp | Val | Asp | Phe | Val | Thr | Asp | Ala | Phe | Thr | Phe | Asn | Asp | Leu |      |
|     |     |     | 585 |     |     |     |     | 590 |     |     |     |     | 595 |     |     |      |
| GGG | ATT | ACA | ACT | TCA | AGT | ACA | AAT | GCT | TTA | TTT | AGT | ATT | TCT | TCA | GAT | 1879 |
| Gly | Ile | Thr | Thr | Ser | Ser | Thr | Asn | Ala | Leu | Phe | Ser | Ile | Ser | Ser | Asp |      |
|     |     | 600 |     |     |     |     | 605 |     |     |     |     | 610 |     |     |     |      |
| AGT | TTA | AAT | TCT | GGA | GAA | GAG | TGG | TAT | TTA | TCG | CAG | TTG | TTT | TTA | GTA | 1927 |
| Ser | Leu | Asn | Ser | Gly | Glu | Glu | Trp | Tyr | Leu | Ser | Gln | Leu | Phe | Leu | Val |      |
|     | 615 |     |     |     |     | 620 |     |     |     |     | 625 |     |     |     |     |      |
| AAA | GAA | TCG | GCC | TTT | ACG | ACG | CAA | ATT | AAT | CCG | TTA | CTA | AAG |     |     | 1969 |
| Lys | Glu | Ser | Ala | Phe | Thr | Thr | Gln | Ile | Asn | Pro | Leu | Leu | Lys |     |     |      |
| 630 |     |     |     |     | 635 |     |     |     |     | 640 |     |     |     |     |     |      |

TAGAAGTCAT GTTAGCACAA GAGGAGTGAG TATTGTGGCT CCTCTTGTAA TTTTAATCGC  2029

TAATATTTCT A  2040

( 2 ) INFORMATION FOR SEQ ID NO:2:

( i ) SEQUENCE CHARACTERISTICS:
        ( A ) LENGTH: 643 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Asp | Ser | Ser | Leu | Asp | Thr | Leu | Ser | Ile | Val | Asn | Glu | Thr | Asp |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Phe | Pro | Leu | Tyr | Asn | Asn | Tyr | Thr | Glu | Pro | Thr | Ile | Ala | Pro | Ala | Leu |
|     |     |     | 20  |     |     |     |     | 25  |     |     |     |     | 30  |     |     |
| Ile | Ala | Val | Ala | Pro | Ile | Ala | Gln | Tyr | Leu | Ala | Thr | Ala | Ile | Gly | Lys |
|     |     |     | 35  |     |     |     |     | 40  |     |     |     |     | 45  |     |     |
| Trp | Ala | Ala | Lys | Ala | Ala | Phe | Ser | Lys | Val | Leu | Ser | Leu | Ile | Phe | Pro |

-continued

|   | 50 |   |   |   |   | 55 |   |   |   |   | 60 |   |   |   |
|---|---|---|---|---|---|---|---|---|---|---|---|---|---|---|
| Gly | Ser | Gln | Pro | Ala | Thr | Met | Glu | Lys | Val | Arg | Thr | Glu | Val | Thr |
| 65 |   |   |   |   | 70 |   |   |   |   | 75 |   |   |   | 80 |
| Leu | Ile | Asn | Gln | Lys | Leu | Ser | Gln | Asp | Arg | Val | Asn | Ile | Leu | Asn | Ala |
|   |   |   |   | 85 |   |   |   |   | 90 |   |   |   |   | 95 |
| Glu | Tyr | Arg | Gly | Ile | Ile | Glu | Val | Ser | Asp | Val | Phe | Asp | Ala | Tyr | Ile |
|   |   |   | 100 |   |   |   |   | 105 |   |   |   |   | 110 |   |   |
| Lys | Gln | Pro | Gly | Phe | Thr | Pro | Ala | Thr | Ala | Lys | Gly | Tyr | Phe | Leu | Asn |
|   |   | 115 |   |   |   |   | 120 |   |   |   |   | 125 |   |   |   |
| Leu | Ser | Gly | Ala | Ile | Ile | Gln | Arg | Leu | Pro | Gln | Phe | Glu | Val | Gln | Thr |
|   | 130 |   |   |   |   | 135 |   |   |   |   | 140 |   |   |   |   |
| Tyr | Glu | Gly | Val | Ser | Ile | Ala | Leu | Phe | Thr | Gln | Met | Cys | Thr | Leu | His |
| 145 |   |   |   |   | 150 |   |   |   |   | 155 |   |   |   |   | 160 |
| Leu | Thr | Leu | Leu | Lys | Asp | Gly | Ile | Leu | Ala | Gly | Ser | Ala | Trp | Gly | Phe |
|   |   |   |   | 165 |   |   |   |   | 170 |   |   |   |   | 175 |   |
| Thr | Gln | Ala | Asp | Val | Asp | Ser | Phe | Ile | Lys | Leu | Phe | Asn | Gln | Lys | Val |
|   |   |   | 180 |   |   |   |   | 185 |   |   |   |   | 190 |   |   |
| Leu | Asp | Tyr | Arg | Thr | Arg | Leu | Met | Arg | Met | Tyr | Thr | Glu | Glu | Phe | Gly |
|   |   | 195 |   |   |   |   | 200 |   |   |   |   | 205 |   |   |   |
| Arg | Leu | Cys | Lys | Val | Ser | Leu | Lys | Asp | Gly | Leu | Thr | Phe | Arg | Asn | Met |
|   | 210 |   |   |   |   | 215 |   |   |   |   | 220 |   |   |   |   |
| Cys | Asn | Leu | Tyr | Val | Phe | Pro | Phe | Ala | Glu | Ala | Trp | Ser | Leu | Met | Arg |
| 225 |   |   |   |   | 230 |   |   |   |   | 235 |   |   |   |   | 240 |
| Tyr | Glu | Gly | Leu | Lys | Leu | Gln | Ser | Ser | Leu | Ser | Leu | Trp | Asp | Tyr | Val |
|   |   |   |   | 245 |   |   |   |   | 250 |   |   |   |   | 255 |   |
| Gly | Val | Ser | Ile | Pro | Val | Asn | Tyr | Asn | Glu | Trp | Gly | Gly | Leu | Val | Tyr |
|   |   |   | 260 |   |   |   |   | 265 |   |   |   |   | 270 |   |   |
| Lys | Leu | Leu | Met | Gly | Glu | Val | Asn | Gln | Arg | Leu | Thr | Thr | Val | Lys | Phe |
|   |   | 275 |   |   |   |   | 280 |   |   |   |   | 285 |   |   |   |
| Asn | Tyr | Ser | Phe | Thr | Asn | Glu | Pro | Ala | Asp | Ile | Pro | Ala | Arg | Glu | Asn |
|   | 290 |   |   |   |   | 295 |   |   |   |   | 300 |   |   |   |   |
| Ile | Arg | Gly | Val | His | Pro | Ile | Tyr | Asp | Pro | Ser | Ser | Gly | Leu | Thr | Gly |
| 305 |   |   |   |   | 310 |   |   |   |   | 315 |   |   |   |   | 320 |
| Trp | Ile | Gly | Asn | Gly | Arg | Thr | Asn | Asn | Phe | Asn | Phe | Ala | Asp | Asn | Asn |
|   |   |   |   | 325 |   |   |   |   | 330 |   |   |   |   | 335 |   |
| Gly | Asn | Glu | Ile | Met | Glu | Val | Arg | Thr | Gln | Thr | Phe | Tyr | Gln | Asn | Pro |
|   |   |   | 340 |   |   |   |   | 345 |   |   |   |   | 350 |   |   |
| Asn | Asn | Glu | Pro | Ile | Ala | Pro | Arg | Asp | Ile | Ile | Asn | Gln | Ile | Leu | Thr |
|   |   | 355 |   |   |   |   | 360 |   |   |   |   | 365 |   |   |   |
| Ala | Pro | Ala | Pro | Ala | Asp | Leu | Phe | Phe | Lys | Asn | Ala | Asp | Ile | Asn | Val |
|   | 370 |   |   |   |   | 375 |   |   |   |   | 380 |   |   |   |   |
| Lys | Phe | Thr | Gln | Trp | Phe | Gln | Ser | Thr | Leu | Tyr | Gly | Trp | Asn | Ile | Lys |
| 385 |   |   |   |   | 390 |   |   |   |   | 395 |   |   |   |   | 400 |
| Leu | Gly | Thr | Gln | Thr | Val | Leu | Ser | Ser | Arg | Thr | Gly | Thr | Ile | Pro | Pro |
|   |   |   |   | 405 |   |   |   |   | 410 |   |   |   |   | 415 |   |
| Asn | Tyr | Leu | Ala | Tyr | Asp | Gly | Tyr | Tyr | Ile | Arg | Ala | Ile | Ser | Ala | Cys |
|   |   |   | 420 |   |   |   |   | 425 |   |   |   |   | 430 |   |   |
| Pro | Arg | Gly | Val | Ser | Leu | Ala | Tyr | Asn | His | Asp | Leu | Thr | Thr | Leu | Thr |
|   |   | 435 |   |   |   |   | 440 |   |   |   |   | 445 |   |   |   |
| Tyr | Asn | Arg | Ile | Glu | Tyr | Asp | Ser | Pro | Thr | Thr | Glu | Asn | Ile | Ile | Val |
|   | 450 |   |   |   |   | 455 |   |   |   |   | 460 |   |   |   |   |
| Gly | Phe | Ala | Pro | Asp | Asn | Thr | Lys | Asp | Phe | Tyr | Ser | Lys | Lys | Ser | His |
| 465 |   |   |   |   | 470 |   |   |   |   | 475 |   |   |   |   | 480 |

| Tyr | Leu | Ser | Glu | Thr 485 | Asn | Asp | Ser | Tyr | Val 490 | Ile | Pro | Ala | Leu | Gln 495 | Phe |
| Ala | Glu | Val | Ser 500 | Asp | Arg | Ser | Phe | Leu 505 | Glu | Asp | Thr | Pro | Asp 510 | Gln | Ala |
| Thr | Asp | Gly 515 | Ser | Ile | Lys | Phe | Ala 520 | Arg | Thr | Phe | Ile | Ser 525 | Asn | Glu | Ala |
| Lys | Tyr 530 | Ser | Ile | Arg | Leu | Asn 535 | Thr | Gly | Phe | Asn | Thr 540 | Ala | Thr | Arg | Tyr |
| Lys 545 | Leu | Ile | Ile | Arg | Val 550 | Arg | Val | Pro | Tyr | Arg 555 | Leu | Pro | Ala | Gly | Ile 560 |
| Arg | Val | Gln | Ser | Gln 565 | Asn | Ser | Gly | Asn | Asn 570 | Arg | Met | Leu | Gly | Ser 575 | Phe |
| Thr | Ala | Asn | Ala 580 | Asn | Pro | Glu | Trp | Val 585 | Asp | Phe | Val | Thr | Asp 590 | Ala | Phe |
| Thr | Phe | Asn 595 | Asp | Leu | Gly | Ile | Thr 600 | Thr | Ser | Ser | Thr | Asn 605 | Ala | Leu | Phe |
| Ser | Ile 610 | Ser | Ser | Asp | Ser | Leu 615 | Asn | Ser | Gly | Glu | Glu 620 | Trp | Tyr | Leu | Ser |
| Gln 625 | Leu | Phe | Leu | Val | Lys 630 | Glu | Ser | Ala | Phe | Thr 635 | Thr | Gln | Ile | Asn | Pro 640 |
| Leu | Leu | Lys |  |  |  |  |  |  |  |  |  |  |  |  |  |

( 2 ) INFORMATION FOR SEQ ID NO:3:

( i ) SEQUENCE CHARACTERISTICS:
                ( A ) LENGTH: 45 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:3:

CGCAGCTCGC GTCGACTCCC GGGTGGAAGA TAGTTCTTTA GATAC        45

( 2 ) INFORMATION FOR SEQ ID NO:4:

( i ) SEQUENCE CHARACTERISTICS:
                ( A ) LENGTH: 40 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:4:

CGATGCTCGC GACAAGTCGA CTCACTCCTC TTGTGCTAAC        40

( 2 ) INFORMATION FOR SEQ ID NO:5:

( i ) SEQUENCE CHARACTERISTICS:
                ( A ) LENGTH: 57 base pairs
                ( B ) TYPE: nucleic acid
                ( C ) STRANDEDNESS: single
                ( D ) TOPOLOGY: linear ( i x ) FEATURE:
                ( A ) NAME/KEY: CDS
                ( B ) LOCATION: 1..57

( x i ) SEQUENCE DESCRIPTION: SEQ ID NO:5:

| ATG | TTT | GAT | ATT | TTT | ACC | CGG | GGA | TCC | GTC | GAC | TCC | CGG | GTG | GAA | GAT | 48 |
| Met | Phe | Asp | Ile | Phe | Thr | Arg | Gly | Ser | Val | Asp | Ser | Arg | Val | Glu | Asp | |
| 1 | | | | 5 | | | | | 10 | | | | | 15 | | |

| AGT | TCT | TTA | | | | | | | | | | | | | | 57 |
| Ser | Ser | Leu | | | | | | | | | | | | | | |

( 2 ) INFORMATION FOR SEQ ID NO:6:

( i ) SEQUENCE CHARACTERISTICS:
( A ) LENGTH: 19 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Phe Asp Ile Phe Thr Arg Gly Ser Val Asp Ser Arg Val Glu Asp
  1               5                  10                 15
Ser Ser Leu
```

RECOMBINANT BIOPESTICIDE AND METHOD OF USE THEREOF

This is a continuation-in-part of application Ser. No. 07/877,876, filed on May 4, 1992, now abandoned.

BACKGROUND OF THE INVENTION

1. Field of the Invention

The present invention relates to an insecticidal protein. More particularly, the invention relates to cloning and expression of the cryIVD gene of *Bacillus thuringiensis* subsp. *israelensis* in certain cyanobacterium and resulting dipteracidal activity.

2. Description of Related Art

Mosquitoes and blackflies are representative of the order Diptera which are pests that have plagued humans and animals for generations. Mosquitoes are the major vectors for a number of human and animal diseases, including malaria, yellow fever, viral encephalitis, dengue fever and filariasis.

Various pesticides have been developed with the hope of controlling Diptera. Unfortunately, many such pesticides are associated with drawbacks which make the search for new pesticides a desirable one. For example, many pesticides exert a broad spectrum of activity and, as a consequence, destroy many non-target organisms which may be beneficial to the environment. Moreover, pesticides are frequently toxic to humans and animals and create environmental hazards in the locus of application.

Biopesticides are a class of naturally occurring pesticides frequently derived from unicellular or multicellular organisms which have developed natural defense against other organisms. The group of microorganisms pathogenic for insects is varied and diverse. The gram-positive soil bacterium *Bacillus thuringiensis* subsp. *israelensis* is one of many *B. thuringiensis* strains able to produce insecticidal proteins. These proteins, expressed during the sporulation cycle of the bacterium, assemble into parasporal crystalline inclusion bodies. The parasporal crystal produced by *B. thuringiensis* subsp. *israelensis* is toxic when ingested by the larvae of Diptera, including mosquitoes and black flies. Upon ingestion, crystal proteins are solubilized in the larval midgut and act in a manner not yet clearly defined to disrupt the epithelium of the larval midgut region. Swelling and/or lysis of the epithelial cells is followed by larval death from starvation.

In the larval stage, many Diptera are filter feeders that feed primarily on microscopic algae and bacteria. In view of these facts and because of the very selective nature of the toxic effects of the *B. thuringiensis* subsp. *israelensis* crystal proteins, there has been interest in employing *B. thuringiensis* subsp. *israelensis* as an agent for Dipter control. There are, however, two major difficulties encountered in attempting to employ *B. thuringiensis* subsp. *israelensis* as both an effective and environmentally safe biolarvicide. First, one protein component of the *B. thuringiensis* subsp. *israelensis* crystal, the cytA gene product, has expressed hemolytic activity in the presence of cultured mammalalian cells. Second, sprayed *B. thuringiensis* subsp. *israelensis* spores demonstrate a limited field life as insecticides, i.e., *B. thuringiensis* strains are not natural competitors in the aquatic environments in which many Diptera breed, and the spores quickly sink out of the upper few decimeters of lakes and streams, where most larval feeding occurs.

In order to overcome both of these difficulties and to present feeding larvae with a continuous pesticide exposure, there has been interest in transferring individual genes coding for nonhemolytic mosquito-toxic *B. thuringiensis* subsp. *israelensis* proteins into bacterial species that could more successfully compete in aquatic larval feeding locales.

Several major polypeptides have been identified as components of the *B. thuringiensis* subsp. *israelensis* insecticidal endotoxin, i.e., polypeptides with molecular mass of 27, 72, and 130 kDa, respectively. The 27 kDa protein is known to be hemolytic, but it is unclear whether the 27 kDa protein is mosquitocidal per se. Although none of the other crystal proteins expresses hemolytic activity, each has been found to exert larvicidal effects on at least some mosquito species.

The gene encoding the 130 kDa protein has been cloned and inserted into both *E. coli* and a cyanobacterium, Synechocystis 6803. See PCT International Pub No. WO 88/06631. Although it is reported therein that transformed Synechocystis 6803 expressed a fusion protein containing the 130 kDa protein, no data is supplied as to the effectiveness of such Synechocytis 6803 as a mosquitocidal.

The gene encoding the 130 kDa protein has also been cloned and inserted into another cyanobacterium, *Agmenellum quadruplicatum* PR-6. See Angsuthanasombat, et al., Appl. Environ. Microbiol. 55:2428–2430 (1989). Although when sonified, the transformed cyanobacterium was found to exert some mosquitocidal activity, the authors state that greater expression of undegraded 130-kDa protein will be necessary for effective control of tropical disease vectors. Other attempts have been made to create an effective dipteracidal cyanobacterium but with little or no success. See Chungjatupornchai, W., Current Microbiology, 21:283–288 (1990). One reason given therein is that the intracellular concentration of mosquidicidal protein is too low for toxic effects to be observed on larval feeding. Moreover, analysis of gel-fractionated cyanobacterial extracts reveals degradation of the expressed protein.

It is known that in translation and expression of proteins preferred codon usage may vary from species to species, i.e., certain species do not translate certain codons which other species routinely translate in making polypeptides. Thus, expression of an exogenous gene introduced from one species to another may be limited by the difference in codon usage observed between the original host of the gene and its new host. For example, preferred codons from *Agmenellum quadruplicatum* PR-6 are different from those of *E. coli* and/or Bacillus. See De Lorimer et al., Proc. Nat. Acad. Sci. USA, Vol. 81, pp. 7946–7950 (1984). Isoleucine encoding AUA codons are not used, or undergo de minimis translation in *Agmenellum quadruplicatum* PR-6. In the one known case of de minimus AUA translation in PR-6, there is no evidence that the protein is actually expressed by the organism. In *Synechococcus elongatus* analysis of the twenty eight known genes indicates no translation of AUA codons. Similarly, analysis of each of the four known genes of Synechococcus sp. WH7803, Synechococcus sp. WH8103 and *Synechococcus vulcanus*, respectively, indicates no translation of AUA codons. In Synechococcus sp. PCC 7942, analysis of the sixty-six known genes indicates de minimus translation of AUA codons, i.e., only four AUA codons out of nearly 1300 other isoleucine encoding codons. In Synechococcus sp. WH8020, one AUA codon is seen in the four known genes which contain thirty-eight other isoleucine encoding proteins. Therefore, it can reasonably be predicted that exogenous genes containing AUA codons could experience translation and expression problems in cyanobacteria. Indeed, failure of the above-described attempts to create an effective dipteracidal may be explained by differences in codon usage between Bacillus and the transformed cyanobacteria.

Thus, a shortcoming in the art has been failure to achieve sufficient expression of intact larvicidal protein in live cyanobacteria to kill Diptera larvae. The present invention overcomes this shortcoming and others and provides a transformant that is lethal to Diptera larvae.

SUMMARY OF THE INVENTION

The present invention provides a recombinant dipteracidal cyanobacterium developed by introducing the diptera-toxic cryIVD gene from *B. thuringiensis* subsp. *israelensis* into the unicellular cyanobacterium *Agmenellum quadruplicatum* PR-6 (synechococcus sp. strain PCC7002). The cryIVD gene is translationally fused to the initial coding sequence of the PR-6 cpcB gene (phycocyanin β subunit coding region), and incorporated into an expression vector.

The present invention further provides a dipteracidal cyanobacterium adapted to proliferate in freshwater to brackish environments.

The present invention also provides a method and means for controlling Diptera, e.g., mosquitoes and blackflies.

BRIEF DESCRIPTION OF THE DRAWINGS

FIG. 2 depicts the nucleotide sequence of cryIVD and the synthesized oligonucleotide primers used to produce the PCR fragment containing the cryIVD gene.

FIG. 3 depicts the 5' portion of the PCR fragment bearing the cryIVD gene following endonuclease restriction with SalI. The fragment carries the entire cryIVD protein coding sequence beginning after the initial methionine codon.

FIG. 4 depicts a translational cpcB-cryIVD gene fusion sequence of plasmid pAQRM56.

DETAILED DESCRIPTION OF THE INVENTION

The present invention is directed to a recombinant cyanobacterium that is lethal to mosquito larvae feeding directly on living cyanobacterial cells. *Agmenellum quadruplicatum* PR-6 (hereinafter "PR-6") is a unicellular cyanobacterium (blue-green alga). Although isolated as a marine species, PR-6 is adaptable, as described below, to fresh water environments. The species is readily transformed and an *E. coli*/PR-6 biphasic expression plasmid has been developed. Plasmid pAQE19ΔSal is based on a fusion between pBR322 and the smallest indigenous PR-6 plasmid pAQ1. Plasmid pAQE19ΔSal carries a strong (phycocyanin operon) PR-6 promoter followed by a multicloning site that begins five codons into the phycocyanin β-subunit coding region of the cpcB gene. Thus, when properly inserted, cryIVD gene expression is under direct control of the strong PR-6 phycocyanin operon promoter in altered strains.

*Agmenellum quadruplicatum* PR-6 has an efficient, well characterized natural DNA uptake system. Transformation of PR-6 with biphasic plasmids has been described (Buzby, J. S. et al., J. Bacteriol. 154:1446 (1983)) More particularly, a biphasic shuttle vector capable of replication and expression of foreign genetic information in *E. coli* and PR-6 is designated plasmid pAQE19LPC and described in U.S. Pat. No. 4,956,280, the contents of which are incorporated herein by reference. *E. coli* containing plasmid pAQE19LPC are on deposit with the American Type Culture Collection, Bethesda, Md. (ATCC No. 68084).

Figure 1:
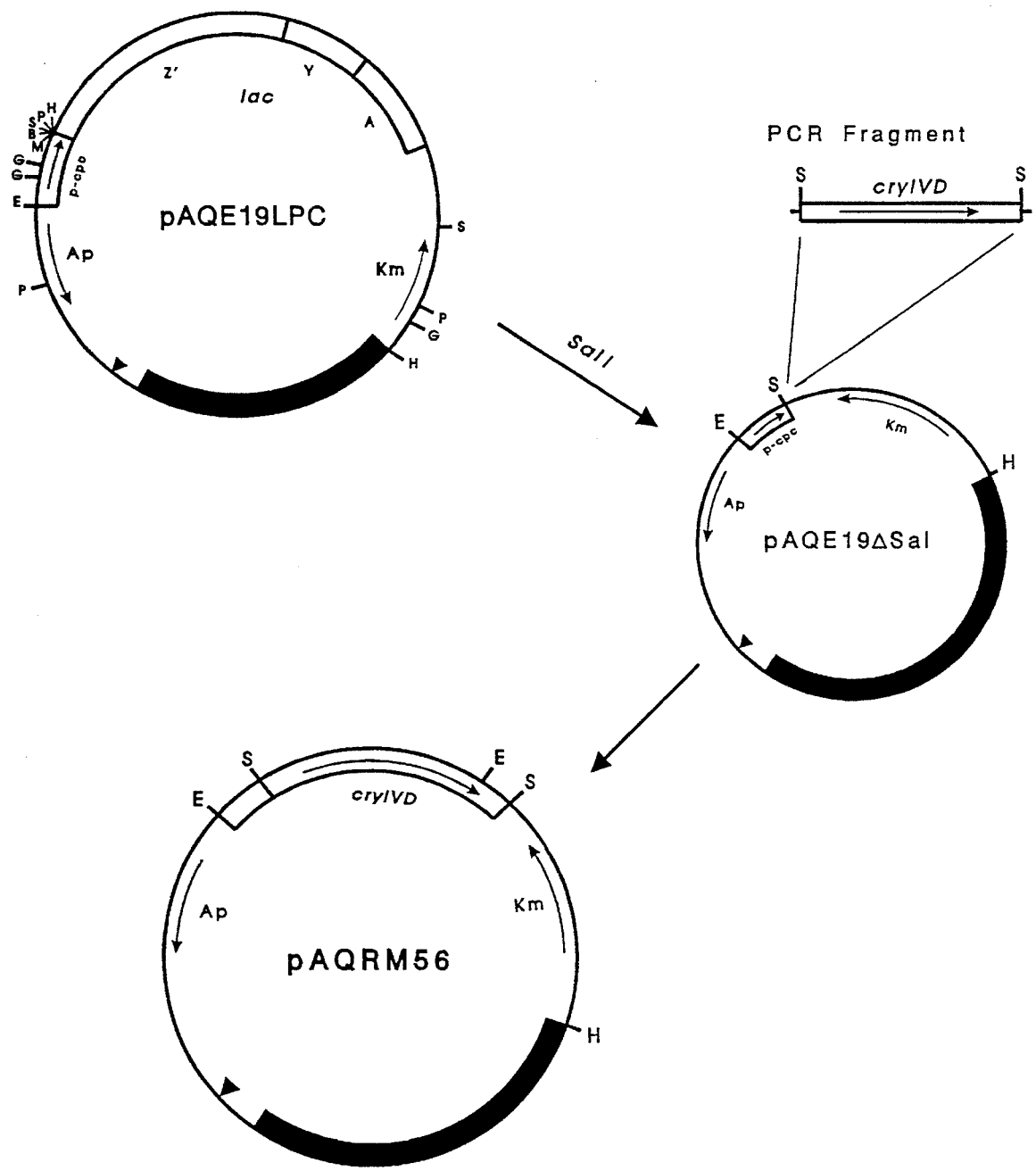
FIG. 1 depicts a scheme for construction of plasmid pAQRM56.

Plasmid pAQRM56 is derived from plasmid pAQE19ΔSal and is a vector employed to transform PR-6 cells into dipteracidal organisms. Construction of pAQRM56 is illustrated in FIG. 1 and is discussed in detail below. Plasmid pEG218 is a pBK derivative harboring the entire *B. thuringiensis* subsp. *israelensis* cryIVD gene which is used as the source of the cryIVD gene.

The present invention involves direct translational fusion, as opposed to transcriptional fusion, between the cyanobacterial cpcB and *B. thuringiensis* subsp. *israelensis* cryIVD genes. Such fusion may be explained as follows: the DNA sequence of any gene can be divided into two portions. First, the protein coding sequence provides the actual instructions for producing a protein of certain length and amino acid composition. Second, the DNA sequence before ("upstream" from) the protein coding sequence is known as a regulatory region that carries information determining when and how much protein will be produced.

In translational fusion, only the protein coding sequence is spliced into another gene, with the result that only one regulatory region is found in the new gene fusion product. In contrast, a transcriptional fusion involves the splicing of a gene, which includes all or part of its own regulatory region, into another gene somewhere after the promoter region of the latter. Thus, a transcriptional fusion carries portions of the regulatory regions from each of the original genes.

Without wishing to be bound by any particular theory, it is believed that transcriptional fusions may result interruption of an integral part of the original regulatory region at the splicing location, thus reducing transcription efficiency. Transcriptional fusions also provide opportunities for the introduction of undesirable regulatory elements that may hinder or prevent expression of the transferred gene. Furthermore, the ribosome binding site is located before the protein coding sequence and a transcriptional fusion of *B. thuringiensis* subsp. *israelensis* genes in cyanobacteria requires that the cyanobacterial ribosome recognize and bind to a Bacillus ribosome site sequence. This is not likely to be an efficient process and further hinders expression of the transferred gene.

In accordance with the present invention, in order to produce a translational fusion between a strong promoter which drives the highly expressed naturally occurring PR-6 cpcB gene and the protein coding region of the cryIVD gene, the splice site of the protein coding sequence must be made at an exact location within the cryIVD gene, i.e., a shift of one base in either direction will result in an alteration of the protein sequence reading frame. The use of a polymerase chain reaction (PCR) allows placement of a restriction site at the exact location required to produce an in-frame translational fusion between the cyanobacterial cpcB and *B. thuringiensis* subsp. *israelensis* cryIVD gene. A translational cpcB-cryI gene fusion sequence is shown in FIG. 4.

The CryIVD gene contains nineteen AUA isoleucine encoding codons which make successful translation and expression in cyanobacterial transformants difficult in view of preferred codon usage by cyanobacteria. See FIG. 2. Thus, the high levels of dipteracidal protein expression and consequent effectiveness of the inventive dipteracidal organisms is indeed surprising.

EXAMPLE 1

Generation of PCR cryIVD Protein Coding Sequence

A 2.0 kbp PCR DNA fragment bearing the entire cryIVD gene was generated from plasmid pEG218 by employing oligonucleotide primers based on the known cryIVD gene sequences. Both primers also carried additional 5' nucleotides bearing SalI endonuclease restriction sites as is shown in FIGS. 2 and 3. The SalI site on the primer bearing the 5' portion of the cryIVD gene was located such that ligation between the SalI restricted PCR fragment and plasmid pAQE19ΔSal, which carries a single SalI site in its multicloning region, would produce the desired in-frame cpcB-cryIVD gene fusion (FIG. 4). The resulting plasmid is pAQRM56. The construction of plasmid pAQRM56 is discussed in greater detail below.

Amplification of the *B. thuringiensis* subsp. *israelensis* cryIVD gene with added flanking restriction sites was done by the procedure of Saiki, et al., Science 230:1350–1354 (1985), by employing a DNA thermal cycler and a DNA amplification reagent kit with Taq polymerase (Perkin-Elmer Cetus Corp., Norwalk, Conn.). Oligonucleotide primers were synthesized on an LKB-Pharmacia Gene Assembler Plus synthesizer. Amplification was allowed to proceed for a total of 25 thermal cycles, with a minimum hybridization temperature of 55° C. Oligonucleotide primers employed for amplification of the cryIVD gene were a 45-mer 5'-CGCAGCTCGCGTCGACTCCCGGGTGGAA-GATAGTTCTTTAGATAC-3' containing a SalI restriction site (nucleotides [nt] 11 to 16) and the second through twenty-third nucleotides of the cryIVD protein coding sequence (nt 24 to 45) and a 40-mer 5'-CGATGCTCGC-GACAAGTCGACTCACTCCTCTTGTGCTAAC-3' containing a SalI restriction site (nt 16 to 21) and 21 nt (nt 20 to 40) complementary to sequence downstream from the cryIVD termination codon (nt 2000 to 1980 of Donovan et al., J. Bacteriol., 170:4732–4738 (1988)).

EXAMPLE 2

Plasmid Construction

Plasmid pAQE19ΔSal is an *E. coli*/PR-6 biphasic expression vector that carries the promoter and initial protein coding sequence of the PR-6 phycocyanin β (cpcB) subunit. A multiple cloning site containing SmaI, BamHI, and SalI restriction sites is located immediately following the initial six codons of the cpcB coding sequence. pAQE19ΔSal is a derivative of the *E. coli*/PR-6 biphasic expression vector pAQE19LPC described in U.S. Pat. No. 4,956,280. Plasmid pAQE19ΔSal, which is based on a fusion between the *E. coli* plasmid pBR322 and the smallest indigenous PR-6 plasmid pAQ1, provides both *E. coli* and PR-6 with resistance to the antibodies ampicillin and kanamycin. Plasmid pAQE19ΔSal also carries the promoter region for the PR-6 phycocyanin operon.

A construction scheme for plasmid pAQRM56 is illustrated in FIG. 1 and includes removal of the lacZ gene from plasmid pAQE19LPC through SalI cleavage and ligation to form plasmid PAQE19ΔSal. The SalI-restricted PCR fragment harboring the *B. thuringiensis* subsp. *israelensis* cryIVD gene was ligated with SalI-restricted pAQE19ΔSal to form plasmid pAQRM56. SalI restricted pAQE19ΔSal was treated with calf intestinal alkaline phosphatase prior to ligation with the PCR generated fragment in order to prevent self ligation of the plasmid. The thick solid line shown in plasmid pAQRM56 indicate PR-6 plasmid pAQ1 sequence. The shaded thick line (p-cpc) indicate regions carrying the PR-6 phycocyanin operon promoter and initial cpcB coding sequence. The arrows give location and orientation of genes coding for ampicillin and kanamycin. Abbreviations used in FIG. 1 are: S=SalI, E=EcoRI, and H=HindIII.

DNA-modifying enzymes and agarose gel electrophoresis were employed using standard procedures (Maniatis, T. E. et al., Molecular cloning: a laboratory manual, Cold Spring Harbor Laboratory (1982)). Restriction endonucleases and T4 DNA ligase were purchased from BRL Life Science Technologies, Inc.; calf intestinal alkaline phosphatase was purchased from Boehringer Mannheim Biochemicals. Small-scale *E. coli* plasmid preparations were done by alkaline lysis (Birnboim, H. C. et al., Nucleic Acids Res. 7:1513–1523 (1979)). Small scale plasmid preparations from PR-6 were done as previously described (Murphy, R. C. et al., J. Bacteriol., 172:967–976 (1990)).

EXAMPLE 3

Transformation of PR-6

The unicellular cyanobacterium PR-6 was maintained in liquid culture in medium A as described in Stevens, S. E. et al., Proc. Natl. Acad. Sci. USA, 77:6052–6056 (1980), the contents of which are incorporated herein by reference. Transformation of PR-6 was carried out as described by Stevens, S. E. et al., supra. The transformation procedure is as follows: nine volumes of recipient cells grown to approximately $4 \times 10^7$ cells per ml were mixed with 1 vol of DNA in 0.15M NaCl/0.015M Na$_3$citrate and incubated for the desired length of time before addition of 1 vol of DNAse I to a final concentration of 10 μg/ml. The cells were then plated on the surface of medium A agar plates and incubated.

Transformants were selected and maintained on media containing ampicillin at concentrations of 2.0 and 4.0 μg/ml, respectively. All PR-6 transformations were verified by back-transforming *E. coli* with PR-6 plasmid isolates followed by restriction analysis of plasmids recovered from the *E. coli* transformants. Restriction analysis verified both insertion of the 2.0-kbp SalI fragment bearing the cryIVD gene and its proper orientation in plasmid pAQE19ΔSal. Two such plasmids, designated pAQRM56a and pAQRM56b, were subsequently employed to transform PR-6. Although both transformed cultures were used in expression and larvicidal assays, there was no discernable difference between the two PR-6 cultures and the two plasmids were subsequently designated pAQRM56.

*E. coli* high-subcloning-efficiency HB101 competent cells were obtained from BRL Life Technologies, Inc., and were used for all *E. coli* plasmid transformations according to the protocol provided. *E. coli* transformants were selected and maintained on 50 and 100 μg of ampicillin per ml, respectively, in Luria-Bertani medium.

EXAMPLE 4

Freshwater Adaptation of Transformed PR-6 Cells

Following transformation, PR-6 cells were adapted to 0% NaCl via successive subculturings in medium A. NaCl concentration was initially 1.8% in medium A and was successively reduced via six stepwise reductions in NaCl, i.e., 0.3% each.

EXAMPLE 5

Expression and Immunological Studies

The predicted molecular mass of the cpcB-cryIVD gene fusion product is 74 kDa. In an attempt to determine whether expression of the protein occurred in transformed PR-6 cells, whole-cell extracts were prepared from cultures of cyanobacterial cells harboring either pAQRM56 or the control plasmid pAQE19ΔSal. Such PR-6 cells were grown in liquid modified (0% NaCl) medium A with 4.0 μg of ampicillin per ml to early stationary phase. One milliliter aliquots were frozen at −20° C. and thawed at room temperature. Cells were harvested by centrifugation, resuspended in lysis solution (50 mM glucose; 25 mM Tris-Cl, pH 8.0; 10 mM EDTA) and allowed to incubate for 5 min at room temperature in the presence of 5 mg of hen egg white lysozyme (Sigma) per ml.

The resulting spheroplasts were microcentrifuged for 1 min at 14,000×g, and the pellet was washed once with 0.1 ml of lysis solution before being resuspended in 0.05 ml of 1 mM phenylmethylsulfonyl fluoride-10 mM EDTA-2% SDS. The samples were frozen at −80° C. for 10 min and thawed at 37° C., and the suspension was twice sonicated for 5 s. NaOH was added to 0.05N, and extracts were maintained at 37° C. for 30 min just prior to the addition of 3.3 volumes of dissociation buffer (60 mM Tris-Cl, pH 6.8; 100 mM dithiothreitol; 2% SDS; 16% glycerol; 0.01% bromophenol blue). Immediately following the addition of dissociation buffer, samples were placed into a boiling water bath for 2 min and cooled to room temperature before 20-μl samples were loaded into gel wells. The polypeptides were site fractionated via SDS-PAGE, i.e., samples were separated by electrophoresis through a 1.5-mm-thick 7.5 to 15% linear gradient polyacrylamide gel (acrylamide/bis-acrylamide, 30:0.8) as described by Laemmli, Nature (London) 227:680–685 (1970) on an LKB 2050 midget electrophoresis unit and the gel was stained with Coomassie brilliant blue.

Figure 5:
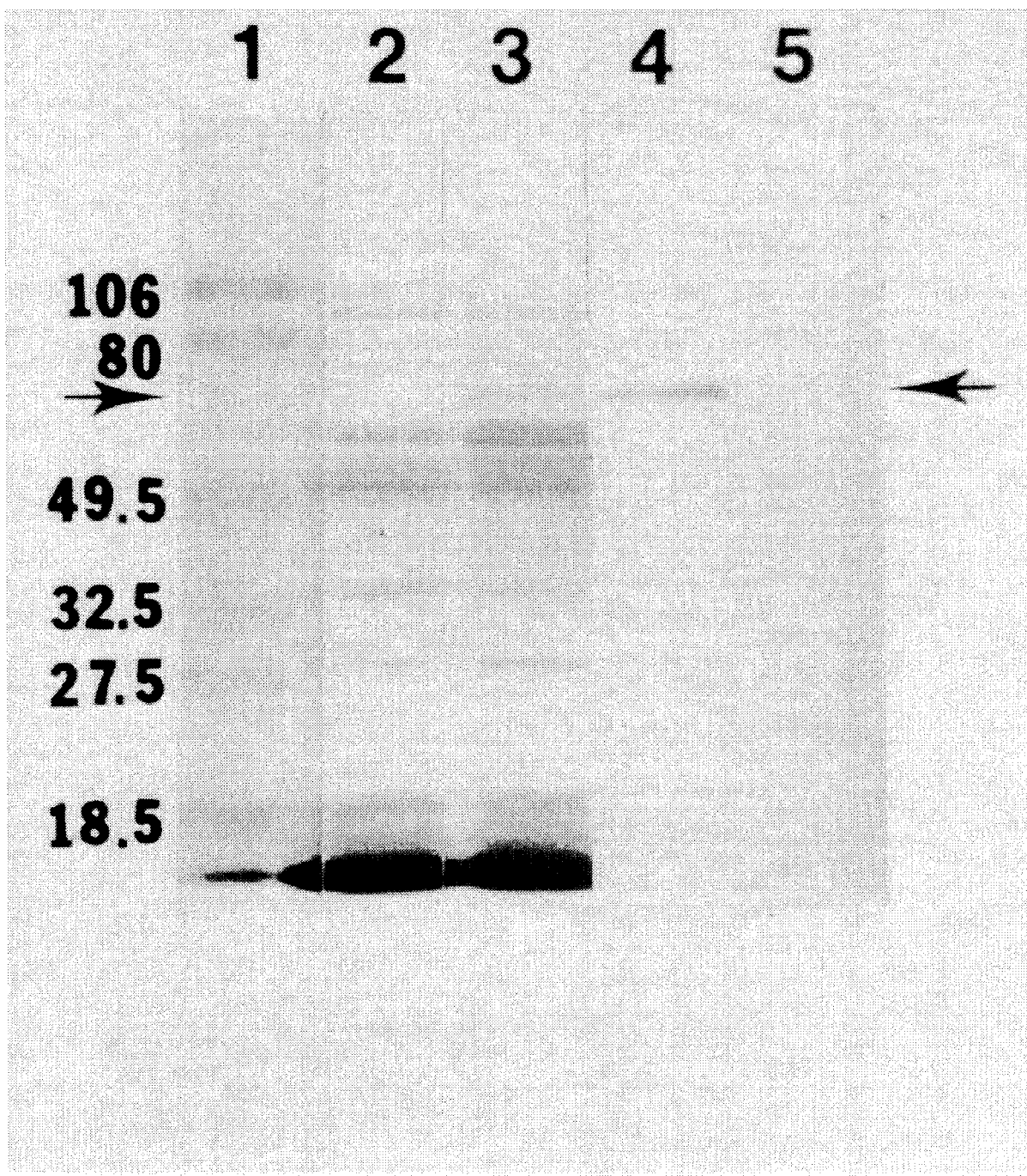
FIG. 5 is a depiction of an SDS/polyacrylamide gel which shows a high level of expression of the 67 kDa protein.

The presence of a 67-kDa polypeptide is clearly evident from extracts of those PR-6 cells harboring plasmid pAQRM56, whereas no such polypeptide is seen in those cells harboring the control plasmid (FIG. 5, lanes 2 and 3). Coumassie brilliant blue-stained polypeptides of whole cell extracts are shown in lanes 2 and 3. Whole cell extracts were prepared from PR-6 bearing plasmids pAQE19ΔSal (lane 2) and pAQRM56 (lane 3). The 67-kDa polypeptide apparently expressed from plasmid pAQRM56 is indicated by the arrows on both sides of FIG. 5. These results are consistent with previous reports that the 72-kDa cryIVD protein shows an apparent molecular mass of 65 to 68 kDa on SDS-polyacrylamide gels. Relative mobilities of the standards (lane 1) are represented in kilodaltons.

Antibodies raised against the *B. thuringiensis* subsp. *israelensis* cryIVD protein were employed to determine whether the observed 67-kDa polypeptide produced in the cyanobacterial cells was antigenically related to the cryIVD protein. Identically loaded but unstained lanes from the same gel were electroblotted onto an Immobilon transfer membrane. Blotted polypeptides from PR-6 bearing pAQRM56 (FIG. 5, lane 4) and pAQE19ΔSal (lane 5) were exposed to mouse polyclonal antiserum directed against the *B. thuringiensis* subsp. *israelensis* cryIVD protein (Ecogen Corporation). Following immunostaining of SDS-PAGE-size-fractionated polypeptides blotted onto the transfer membrane, the transfer paper was immunostained by the procedure suggested by Amersham for immunogold staining with their Auroprobe BLplus gold-labelled goat anti-mouse immunoglobulin G plus immunoglobulin M (H+L) as secondary antibody. The mouse anitsera raised against the *B. thuringiensis* subsp. *israelensis* cryIVD protein (Ecogen Corporation) was diluted 500-fold prior to use.

A single strong signal coincidental with the Coomassie brilliant blue-stained 67kDa polypeptide was observed in those PR-6 cells harboring plasmid pAQRM56 (FIG. 5, lane 4); no signal was detectable in PR-6 cells carrying the control plasmid (lane 5). Both the observation that PR-6 cells harboring plasmid pAQRM56 produce a polypeptide not observed in extracts of PR-6 cells carrying plasmid pAQE19ΔSal and the finding that this polypeptide retains the antigenic integrity of the *B. thuringiensis* subsp. *israelensis* cryIVD protein indicate that these cyanobacterial cells are in fact expressing the cpcB-cryIVD gene fusion provided by the presence of plasmid pAQRM56.

EXAMPLE 6

Larvicidal Assays

*Culex piptens* mosquito larvae hatched in the laboratory were observed to readily ingest both wild-type and pAQE19ΔSal-bearing PR-6 cells and were found to be able to pupate and emerge as adults when these cyanobacteria were provided as the sole food source. In order to determine whether cyanobacterial cells expressing the cpcB-cryIVD gene fusion product could prove to be lethal to mosquito larvae feeding on the cells, newly hatched mosquito larvae were separated and fed either wild-type or pAQRM56-bearing PR-56 cells as described below.

Figure 6:
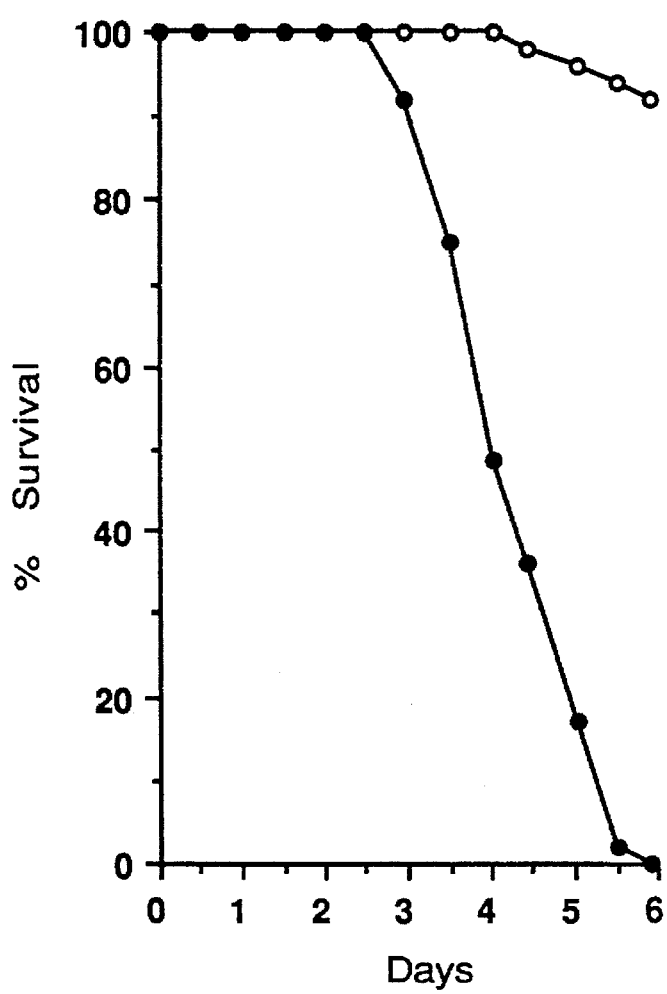
FIG. 6 depicts survival rates of *Culex pipens* mosquito larvae fed either wild-type (o) or pAQRM56-bearing (●) PR-6 cells.

Adult female *Culex pipens* mosquitoes were obtained and allowed to lay eggs in a glass petri dish containing 40 ml of distilled water. After hatching, larvae were separated and placed into individual microliter wells in 96-well culture dishes; each well contained 0.25 ml of distilled water and one larva. Between feedings, culture dishes were covered with plastic wrap to reduce evaporation. PR-6 cultures were grown to stationary phase, harvested by centrifugation, washed once in a modified medium A (0% NaCl), and restored to their original volume in fresh modified medium A. At each feeding, all live larvae were provided with 3.0 to 5.0 μl of the washed PR-6 cells. Feeding occurred at 12-h intervals, with alternate wells in each microliter plate receiving control (wild-type or pAQE19ΔSal-bearing PR-6 cells) or pAQRM56-bearing PR-6 cells. The total number of larvae represented in FIG. 6 is 191; 96 larvae were fed wild-type cells and 95 larvae were fed transformed PR-6 cells. Just prior to each feeding, all larvae were observed in situ under a dissection microscope to check for viability and, if the larva was alive, the general condition of the larva.

Initially, the newly hatched *C. pipiens* larvae readily ingested both wild-type and pAQRM56-bearing PR-6 cells. However, within 2 days those larvae feeding on the pAQRM56-bearing cells began to stop feeding, became sluggish and nonresponsive to physical probing, and displayed internal structural deformities in the midgut region that occasionally resulted in complete disruption of the body cavity. Although microscopic observation revealed that many larvae remained alive in such a state for several days, all of these larvae died within 6 days of hatching (FIG. 6). In contrast, more than 90% of the control larvae remained alive, continuing to feed and maintain a healthy appearance throughout the same period.

A similar experiment (terminated after 4 days) utilizing pAQE19ΔSal-bearing PR-6 cells as controls yielded almost identical results; 4 days after hatching, 94% (90 of 96) of larvae fed pAQE19ΔSal-bearing cells were alive versus 51% (49 of 96) of larvae fed pAQRM56-bearing cyanobacterial cells. In both experiments, it was noted that those control larvae that died did not present symptoms similar to those observed for larvae fed the pAQRM56-bearing cyanobacteria. Rather, these larvae appeared generally healthy and active at one feeding but were found dead 12 h later.

The examples and embodiments depicted in this specification are not intended to be limitations on the inventive concept described herein. For example construction of plasmids by restriction and ligation is well known in the art and, consequently, plasmids of construction other than those depicted herein are within the scope of the present invention as long as a gene encoding dipteracidal protein is translationally fused to a strong native cyanobacterial promoter within vectors used to transform target cells. Examples of such promoters include cpc genes (rod components for the phycobilisome), apc genes (core components for the phycobilisome), rbc genes (large and small subunits of ribulose bisphosphate carboxylase/oxygenase), atp genes (structural genes for the ATP synthase protein complex), psb genes (structural genes for the photosystem II complex), psa genes (structural genes for the photosystem I complex), and pet genes (cytochrome and ferredoxin genes).

Likewise, photoautotrophs other than PR-6 are within the scope of the present invention. For example *Agmenellum quadruplicatum BG*-1 (Synechococcus 73109) (ATCC 29404), *Coccochloris elabens* 17-A (Synechococcus 7003) (ATCC 27265), Aphanocapsa (Synechocystis 6714) (ATCC 27178), *Nostoc muscorum* UTEX 1545 (Nostoc 6314) (ATCC 27904), Nostoc sp. MAC (Nostoc 73102) (ATCC 29133), *Chloroglea fritschii* (*Chlorogloeopsis fritschii*) (Chlorogloeopsis 6912) (ATCC 27193), *Anabaena flos* (aquae) (ATCC 22664), and *Anabaena variabilis* (Anabaena 7118) (ATCC 27892) are all suitable. Accordingly, one with skill in the art may make modifications in the methods and products which are intended to be covered by the following claims.

What is claimed is:

1. A DNA construct comprising a phycocyanin β promoter operably linked to a B. thuringiensis subsp. israelensis cryIVD protein coding sequence.

2. A DNA construct according to claim 1 wherein the phycocyanin β promoter is translationally fused with the B. thuringiensis subsp. israelensis cryIVD protein coding sequence.

3. A transformation vector comprising a DNA construct according to claim 2.

4. A transformation vector according to claim 3 wherein said transformation vector is a plasmid.

5. A cell transformed by a transformation vector according to claim 3.

6. A cell transformed by a transformation vector according to claim 4.

7. A biologically functional plasmid comprising an E. coli replication origin, an A. quadruplicatum replication origin, at least one selectable marker and a phycocyanin β promoter operably linked to a B. thuringiensis subsp. israelensis cryIVD protein coding sequence.

8. A biologically functional plasmid according to claim 7 wherein the phycocyanin β promoter is translationally fused with the B. thuringiensis subsp. israelensis cryIVD protein coding sequence.

9. A cyanobacterial host transformed by a plasmid according to claim 7.

10. A cyanobacterial host according to claim 9 wherein said cyanobacterial host is selected from the group consisting of Agmenellum quadruplicatum BG-1 (Synechococcus 73109) (ATCC 29404), Coccochloris elabens 17-A (Synechococcus 7003) (ATCC 27265), Aphanocapsa (Synechocystis 6714) (ATCC 27178), Nostoc muscorum UTEX 1545 (Nostoc 6314) (ATCC 27904), Nostoc sp. MAC (Nostoc 73102) (ATCC 29133), Chloroglea fritschii (Chlorogloeopsis fritschii) (Chlorogloeopsis 6912) (ATCC 27193), Anabaena flos (aquae) (ATCC 22664), and Anabaena variabilis (Anabaena 7118) (ATCC 27892).

11. An A. quadruplicatum host transformed by a plasmid according to claim 7.

12. A bacterial host transformed by a plasmid according to claim 7.

13. An insecticide suitable for use against Diptera comprising a cyanobacterial host transformed by a plasmid according to claim 7.

14. An insecticide suitable for use against Diptera comprising an A. quadruplicatum host transformed by a plasmid according to claim 8.

15. A method of killing Diptera larvae comprising introducing an insecticidally effective amount of A. quadruplicatum hosts transformed by a plasmid according to claim 8 in an environment containing Diptera larvae.

16. An A. quadruplicatum host according to claim 11 adapted to survive in a freshwater environment.

17. An A. quadruplicatum host according to claim 11 adapted to survive in a brackish water environment.

18. An A. quadruplicatum host according to claim 16 wherein said host is adapted to survive in fresh water environments by successive liquid subculturings in a medium containing 0.3% stepwise reductions in NaCl concentration.

19. A biologically functional plasmid comprising an A. quadruplicatum replication origin, at least one selectable marker and a phycocyanin β promoter operably linked to a B. thuringiensis subsp. israelensis cryIVD protein coding sequence.

20. A biologically functional plasmid according to claim 19 wherein the phycocyanin β promoter is translationally fused with the B. thuringiensis subsp. israelensis cryIVD coding sequence.

21. A biologically functional plasmid comprising on E. coli replication origin, and A quadruplicatum replication origin, at least one selectable marker and a cyanobacterial promoter for a protein selected from the group consisting of cpcB, apc, rbc, atp, psb, psa, and pet, translationally fused with the B. thuringiensis subsp. israelensis cryIVD protein coding sequence.

22. A cyanobacterial host transformed by a biologically functional plasmid according to claim 21 wherein said cyanobacterial host is selected from the group A. quadruplicatum PR-6, Agmenellum quadruplicatum BG-1 (Synechococcus 73109) (ATCC 29404), Coccochloris elabens 17-A (Synechococcus 7003) (ATCC 27265), Aphanocapsa (Synechocystis 6714) (ATCC 27178), Nostoc muscorum UTEX 1545 (Nostoc 6314) (ATCC 27904), Nostoc sp. MAC (Nostoc 73102) (ATCC 29133), Chloroglea fritschii (Chlorogloeopsis fritschii) (Chlorogloeopsis 6912) (ATCC 27193), Anabaena flos (aquae) (ATCC 22664), and Anabaena variabilis (Anabaena 7118) (ATCC 27892).

23. A method for recombinantly deriving a dipteracidal microorganism comprising:

(i) isolating a B. thuringiensis subsp. israelensis cryIVD protein coding sequence;

(ii) forming a plasmid containing a native cyanobacterial regulatory gene sequence;

(iii) translationally fusing the B. thuringiensis subsp. israelensis cryIVD protein coding sequence with the native cyanobacterial regulatory gene sequence contained in the plasmid;

(iv) transforming a microorganism with the plasmid according to step (iii); and (v) growing the microorganism of step (iv) whereby the B. thuringiensis subsp. israelensis cryIVD protein is expressed in said microorganism.

24. A method for recombinantly deriving a dipteracidal microorganism according to claim 23 wherein said microorganism is a cyanobacterium.

25. A method for recombinantly deriving a dipteracidal microorganism according to claim 24 wherein said cyanobacterium is *Agmenellum quadruplicatum*.

26. A method for recombinantly deriving a dipteracidal microorganism according to claim 23 wherein said microorganism is *E. coli*.

27. A method for recombinantly deriving a dipteracidal microorganism according to claim 23 wherein said native cyanobacterial regulatory gene sequence is a *A. quadruplicatum* PR-6 cpcB regulatory gene sequence.

28. A method for recombinantly deriving a dipteracidal microorganism according to claim 23 wherein said plasmid according to step (iii) is pAQMR56.

29. A DNA construct comprising a phycocyanin β promoter operably linked to a *B. thuringiensis* subsp. *israelensis* cryIVD protein coding sequence wherein said cryIVD protein coding sequence contains at least one AUA codon.

30. A cyanobacterial cell containing a DNA construct according to claim 29.

* * * * *